(12) United States Patent
Callede et al.

(10) Patent No.: US 9,072,508 B2
(45) Date of Patent: Jul. 7, 2015

(54) DEVICE FOR TAKING AT LEAST ONE SAMPLE OF TISSUE

(75) Inventors: David Callede, Sarlar la Caneda (FR); Denis Pinaud, Draillant (FR); Adrien Moine, Evian (FR); Laurent Pivard, Dortan (FR); Fabrice Teppe, Oyonnax (FR)

(73) Assignee: Coloplast A/S, Humlebaek (DK)

( * ) Notice: Subject to any disclaimer, the term of this patent is extended or adjusted under 35 U.S.C. 154(b) by 153 days.

(21) Appl. No.: 13/809,911

(22) PCT Filed: Jul. 15, 2011

(86) PCT No.: PCT/DK2011/050283
§ 371 (c)(1),
(2), (4) Date: Jan. 14, 2013

(87) PCT Pub. No.: WO2012/007010
PCT Pub. Date: Jan. 19, 2012

(65) Prior Publication Data
US 2013/0116595 A1 May 9, 2013

(30) Foreign Application Priority Data

Jul. 16, 2010 (EP) ..................................... 10290405
Oct. 25, 2010 (EP) ..................................... 10188673

(51) Int. Cl.
*A61B 10/00* (2006.01)
*A61B 10/02* (2006.01)
*A61B 17/00* (2006.01)

(52) U.S. Cl.
CPC ..... *A61B 10/0275* (2013.01); *A61B 2010/0208* (2013.01); *A61B 2017/00367* (2013.01); *A61B 2017/00393* (2013.01)

(58) Field of Classification Search
USPC ................... 600/562, 564, 567; 606/167, 170
See application file for complete search history.

(56) References Cited

U.S. PATENT DOCUMENTS

| 4,958,625 | A | 9/1990 | Bates et al. |
| 5,842,999 | A | 12/1998 | Pruitt et al. |
| 7,153,275 | B2 | 12/2006 | Blondeau |
| 2004/0097830 | A1 | 5/2004 | Cooke et al. |

*Primary Examiner* — Brian Szmal
(74) *Attorney, Agent, or Firm* — Coloplast Corp., Coloplast A/S; Nick Baumann

(57) ABSTRACT

This invention relates to a device (10) for taking at least one sample of soft tissue from an organ, said device comprising a body (11) and a needle (12) arranged in the body and extending at least partly outside the body through the front end of the body, the needle is formed by a stylet and a cannula coaxial with said stylet. The device comprises a mechanism for arming the needle, designed for sequentially moving the stylet and then the cannula from a rest position to a shooting position wherein the stylet and the cannula are retracted towards the rear end of the body, and a triggering mechanism designed to release the stylet then the cannula and to allow their displacement from the shooting position to the rest position. The cannula is coupled to a cannula slider (24) comprising at least one retaining element (26) for maintaining the cannula slider in a shooting position. The stylet is coupled to a stylet slider (30) comprising at least one retaining element (32) for maintaining the stylet slider in a shooting position and means for unlocking the cannula slider. This device is characterized in that the stylet slider (30) comprises a support device (41) integral with the stylet and a guide device (42) mobile in the body (11) of the device, in that the displacement of the guide device (42) leads to the displacement of the support device (41) and in that the support device (41) and the guide device (42) have a clearance between each other.

11 Claims, 3 Drawing Sheets

DEVICE FOR TAKING AT LEAST ONE SAMPLE OF TISSUE

TECHNICAL FIELD

The present invention relates to a device for taking at least one sample of soft tissue from an organ, said device comprising a body and a needle arranged in the body and extending at least partly outside the body through the front end of the body, the needle is formed by a stylet and a cannula coaxial with said stylet, said device comprising a mechanism for arming the needle, designed for sequentially moving the stylet and then the cannula from a rest position to a shooting position wherein the stylet and the cannula are retracted towards the rear end of the body, and a triggering mechanism designed to release the stylet then the cannula and to allow their displacement from the shooting position to the rest position, the cannula being coupled to a cannula slider comprising at least one retaining element for maintaining the cannula slider in a shooting position, the stylet being coupled to a stylet slider comprising at least one retaining element for maintaining the stylet slider in a shooting position and means for unlocking the cannula slider.

BACKGROUND ART

Nowadays, there are several devices for taking samples of soft tissue, these devices being generally used to extract, in a minimally invasive way, a sample of an organ from a human being or an animal for analysis purpose. This extraction operation is generally known as biopsy and the device used is known as a biopsy gun.

Such a sampling device comprises, in particular, a sampling needle formed by a cannula and a stylet, an arming mechanism placed on a body and a trigger also placed on the body of the device.

The arming mechanism is used to partially retract the needle towards the inside of the body of the device. The device is placed near the organ from which a sample is to be taken, and then the trigger is pressed so that the needle can penetrate into the organ. The needle being formed by a stylet and by a cannula, the stylet penetrates into the organ, then the cannula covers the stylet. The stylet comprises at least one notch receiving the tissue sample to be taken. When the cannula covers the stylet, the tissue sample is trapped in the notch and is cut. The unit is withdrawn so that the sample(s) arranged between the stylet and the cannula can be removed. An example of application of such a device is taking tissue samples from the prostate.

The arming of the needle is generally achieved in two steps, namely the arming of the cannula in a first step and the arming of the stylet in a second step.

During sampling of tissues, it is common for the person carrying out the sampling to have only one free hand, while the other hand is being used to hold other medical devices, such as for example an echographic probe. In this case, it is important to be able to handle the sampling device with one single hand. Here, the handling includes the arming of the cannula, the arming of the stylet and the release of the shot allowing the sample to be taken.

An example of existing devices, which enable handling with one single hand, is described in U.S. Pat. No. 7,153,275. This device is perfectly functional in most cases. However, problems may occur in certain circumstances. These problems may arise from the fact that the stylet and the cannula are not perfectly aligned and the stylet does not slide in a totally optimal way in the cannula. Indeed, an optimal sliding motion involves particularly tight manufacturing tolerances when manufacturing the parts of the biopsy gun. These tolerances can sometimes be difficult to maintain on parts made from plastic. This may lead to jamming of the needle, sometimes even deformation. A further consequence is the reduction in the number of shots that can be carried out with a device.

In order to minimize the problems linked to the jamming of the stylet in the cannula, a relatively powerful spring is used for the cannula in order to propel the latter in an effective way. This has the drawback that a greater force is required to arm the device, which is undesirable for the user. Despite such a spring, the needle may jam and bend so that the device becomes unusable.

The following description describes a tissue sampling device which has the advantages of the devices of the prior art, i.e. it is possible to use this device with one hand. However, this device does not have the drawbacks of the systems of the prior art. Thus, the risk of jamming of the needle, as well as the risk of breakage or deformation, is strongly reduced or even eliminated.

DISCLOSURE OF THE INVENTION

An object of the invention is fulfilled by a sampling device as defined in the preamble and characterized in that the stylet slider comprises a support device integral with the stylet and a guide device moveable along a guide rail provided in the body of the device, in that the displacement of the guide device leads to the displacement of the support device and in that the support device and the guide device have a clearance between each other.

According to the present invention, the device for taking samples may easily be handled with one hand. To achieve this, the device comprises a body having an essentially cylindrical shape that can be easily held. It also comprises a sliding arming button, which is positioned on the body so that this button can be easily moved using one finger. The arming button is connected to an arming mechanism, which has two different functions. In a first step, the displacement of the arming button has the effect of moving the cannula towards the back of the body. When the cannula has been displaced to the desired position, the arming button is released, allowing it to return to its initial position. When it is operated again, the arming button has a different function than the previous one. In a second step, it is used to move the stylet towards the back of the body. Owing to the mechanism of the invention, the user carries out the same displacement movement of the arming button twice, these two movements having different effects.

This way of proceeding has the advantage of enabling the realization of a body of relatively small length, thus only requiring a displacement of the arming button, which is compatible with the displacement of the user's finger, without the user having to change the position of his/her hand. The slider of the stylet is made in such a way that the cannula slides relatively easily along the stylet, irrespective of the tolerances between the pieces forming the biopsy gun. To achieve this, the stylet is maintained in the body of the biopsy gun in order to present a certain clearance in relation to the body, assuring a precise guidance of the cannula along the stylet. This is obtained by decoupling the function of support of the cannula and the function of guidance in the body and by ensuring a certain space between the devices in charge of these two functions. By means of this decoupling it is possible to avoid the problems related to the fact that the stylet slider of the devices of prior art is hyperstatic. With such a system, one increases the displacement range in two directions (up/down;

left/right), without increasing the clearance in the axis of the needle. Thus, the displacement along this axis of the needle is not affected, and the stylet is self-centred in relation to the cannula.

The device of the invention makes it possible to avoid jamming of the stylet and the cannula, as well as the possible consequences of it, such as deformation or rupture.

By virtue of the geometry of the device, the elements which enable the guidance of the stylet and the cannula, as well as the propulsion and retaining elements for the stylet and the cannula are arranged symmetrically around a longitudinal axis materialized by the stylet. This ensures that there are few transversal forces. Such transversal forces have the effect of increasing the friction between the parts, of causing wear and of risks of rupture as well as of jamming. By suppressing these transversal forces, it is possible to use smaller springs, as it is no longer necessary to overcome friction. The biopsy gun is thus easier to use, since the arming is made easier. Moreover, more samples may be taken using the gun, since the jamming risk is reduced.

BRIEF DESCRIPTION OF THE DRAWINGS

This invention and its advantages will be better understood with reference to the enclosed drawings and to the detailed description of a particular embodiment, in which.

BEST MODE FOR CARRYING OUT THE INVENTION

Figure 1:
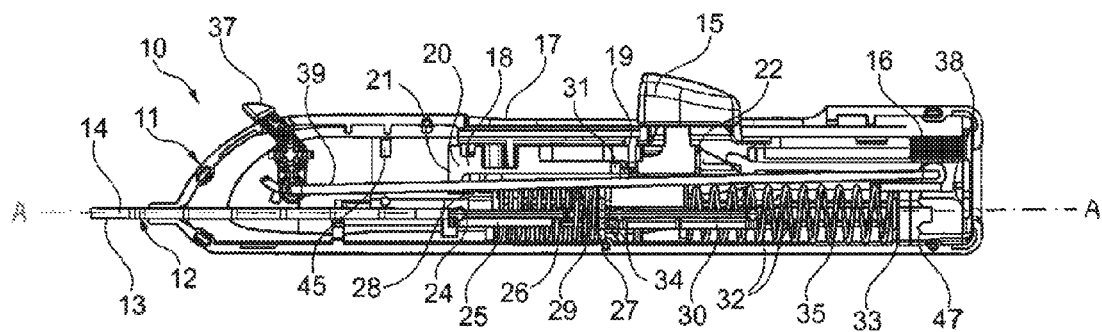
FIG. 1 is an overview of the device of the present invention.
Figure 2:
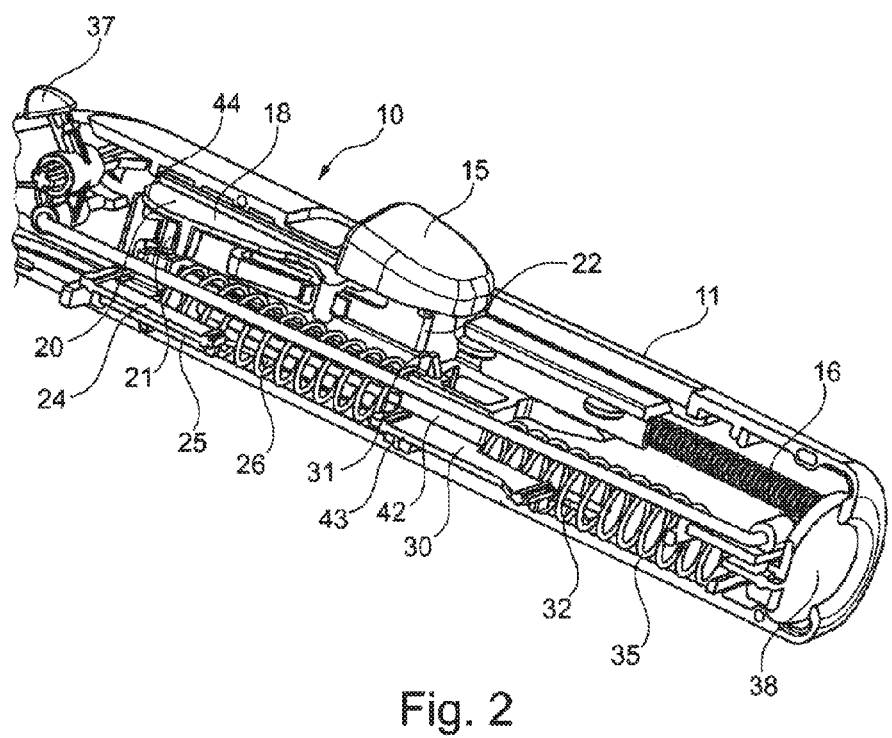
FIG. 2 represents a detail of the device of FIG. 1.

With reference to the drawings, the sampling device 10 according to this invention essentially comprises a body 11 and a needle 12. The needle is formed by a stylet 13 and a cannula 14. The stylet comprises a tip, allowing the needle to penetrate into the organ from which one wishes to take a sample. Furthermore, the stylet comprises at least one notch (not shown). In practice, the stylet 13 comprises a notch that enables a sample to be taken. The cannula 14 slides around the stylet 13 and is used on one hand to cut the tissue into which the stylet has penetrated and on the other hand to keep the tissue sample in place when removing the needle from the organ.

The body 11 essentially comprises an arming mechanism arranged to arm the needle 12 and a triggering device arranged to release a shot of the needle for the intended sampling. More particularly, the arming of the needle is carried out in two steps, namely a step of arming the cannula 14 and a step of arming the stylet 13.

The sampling is made by a shot of the needle. Such a shooting also comprises two steps, namely a displacement step of the stylet 13 under the effect of a propelling power of the stylet, then a displacement step of the cannula 14 under the effect of a propelling power of the cannula. Releasing a shot is achieved by releasing the displacement of the stylet. The displacement of the cannula is a consequence of the release of the stylet as it will be explained in detail below.

In practice, the mechanism for arming the cannula and the mechanism for arming the stylet use only one arming button 15 which acts differently depending on whether the arming of the cannula has already been carried out or not. This arming button cooperates with a return spring 16 of the arming button, the spring having the function of bringing back the arming button 15 to the rest position, i.e. towards the front of the body, when it is not manipulated.

The body of the device is formed by two parts which, once assembled, comprise guidance grooves intended to ensure the displacement of the parts. The body also comprises a slit 17 in which the arming button moves.

With reference to the figures, the arming button 15 cooperates with a platform 18. The platform can pivot around a platform axis 19 integral with the arming button. One of the ends of the platform, located near the front end of the sampling device, i.e. the needle-end of the sampling device, comprises a widened zone 20, each end of this widened zone including a finger 21 whose function is described in detail below. The rear end of the platform comprises a pushing device 22 whose function is also described in detail below.

The platform 18 is connected to the arming button 15 by the platform axis 19 and by a return device (not shown). This return device may be a spring or an elastic tab which has the function of keeping this platform in a predefined position called a rest position.

The mechanism for arming the cannula 14 is intended to move the cannula into the shooting position. This cannula is coupled to a cannula slider 24. According to one advantageous embodiment, the cannula slider 24 comprises two fins 25 disposed in a plane also containing the cannula. These two fins 25 cooperate with two guide grooves provided in the body of the device so as to ensure an effective sliding motion of the cannula slider 24. This slider comprises, at its rear end, a retaining element 26 of the cannula slider. According to an advantageous embodiment, the retaining element is formed by two hooks. Advantageously, these hooks are symmetrical and have a certain flexibility, which allows for them to be hooked onto a retaining device 27 of the cannula slider and to be unhooked from this device by bringing the hooks together. It is also possible to use only one hook or several hooks arranged asymmetrically.

Furthermore, the cannula slider 24 comprises a spur 28 cooperating with one of the fingers 21 of the platform. The cannula slider cooperates with a spring 29 for the propulsion of the cannula slider, which is arranged between the cannula slider 24 and the retaining device 27 of the cannula slider. This spring 29 is designed to supply the required force to propel the cannula slider towards the front of the body. The displacement of the cannula slider towards the back of the body compresses the spring.

The mechanism for arming the stylet is intended for the displacement of the stylet 13 into the shooting position, this displacement being achieved after the cannula 14 has been armed. To that effect, the stylet 13 is coupled to a stylet slider 30.

This stylet slider comprises two parts, namely a support device 41 and a guide device 42. The support device 41 is integral with the stylet 13. According to a particular embodiment, it is overmolded on the stylet. The guide device 42 comprises fins 43 cooperating with guide grooves provided in the body 11 of the device. The guide device has such a configuration that the displacement of the guide device 42 leads to the displacement of the support device 41. However, a clearance perpendicular to the longitudinal axis A-A defined by the length of the needle is provided between the support device 41 and the guide device 42. This clearance enables a relative displacement of the support device 41 in comparison with the guide device 42 in a plane substantially perpendicular to the needle. By means of this clearance it is possible to take into account the manufacturing tolerances of the different elements of the device of the invention. The support device 41 is in a "suspended" setup in comparison with the guide device 42. Little or no clearance exists along the longitudinal axis A-A defined by the needle.

The guiding device 42 comprises a spur 31 near its front end and a retaining element 32 at its rear end. Like for the cannula slider, the retaining element 32 can be formed by two partially elastic hooks. It can also be formed by only one hook or by several hooks arranged symmetrically or asymmetrically.

The retaining element 32 can be hooked on a retaining device 33 of the stylet slider and can be unhooked from this device by approaching the hooks to each other.

Similar to the cannula slider, the hooks of the stylet slider are sufficiently flexible to be deformed towards each other and sufficiently rigid to provide adequate support.

The stylet slider 30 comprises, at its front end, i.e. at the side of the cannula slider, unlocking means 34 formed, for example, by two inclined planes.

The guide device 42 of the stylet slider cooperates with a spring 35 for the propulsion of the stylet slider, which is placed between the stylet slider 30 and the retaining device 33 of the stylet slider. The spring is designed to supply the required force to propel the stylet slider 30 towards the front of the body and unlock the cannula slider. The displacement of the stylet slider towards the back of the body compresses the spring.

The device according to the invention further comprises a triggering device. According to an advantageous embodiment, this triggering device comprises two triggers 37, 38 connected to each other by a rod 39. One of the triggers 37 is placed in the front of the body, in front of the arming button 15, and the other trigger 38 is placed in the rear of the body. The rear trigger 38 is associated with a return spring of the trigger, designed to bring the trigger back in the original position after it has been pressed.

The rear trigger 38 comprises means 47 for unlocking the stylet slider formed by two elements arranged in inclined planes.

The sampling device according to this invention operates in the following way. Let us suppose that the initial position is a position in which the cannula 14 and the stylet 13 are maximally extended towards the outside of the body 11 of the device. This position corresponds to the normal position of the device when it is not going to be used, i.e. the rest position.

In a first step, the arming of the cannula 14 is carried out. During this operation, the user actuates the arming button 15, sliding it towards the back of the device 10. The platform 18 being integral with the arming button 15, the displacement of the latter also draws the platform backwards. One of the fingers 21 of the platform 18 comes in contact with the spur 28 placed towards the front end of the cannula slider 24. The latter is thus displaced backwards, against the force of the spring 29 for the propulsion of the cannula slider. This movement is carried out until the retaining elements 26 of the cannula slider 24 enter into contact with the retaining device 27 for the cannula slider. The retaining elements of the cannular 24 may be formed as hooks and the retaining device 27 may for example be a ring provided in the body of the device. The ring comprises a central hollow in which the ends of the hooks of the cannula slider pass. These hooks lean on the back face of the ring and maintain the cannula slider 24 in place against the force of the propulsion spring of the cannula slider.

When the arming of the cannula is completed, the arming button 15 is released. It returns to its initial position towards the front of the device, under the effect of the return spring 16 of the arming button.

During the forward displacement of the platform 18, following the forward displacement of the arming button 15, a ramp 44 of the platform comes into contact with a plug 45 provided in the body. The ramp 44 has the effect of rotating the platform 18 around the platform axis 19, against the force of a return device of the platform. It should be noted that according to this embodiment, it is also possible to provide for the return device of the platform to be constrained before the arming of the cannula and to be released when the arming of the cannula is completed.

For the arming of the stylet 13, the arming button 15 is displaced backwards again. However, the platform 18 is no longer in the initial position. The latter has pivoted around the platform axis 19, as the ramp 44 of the platform has been displaced by the support against the plug 45. By this rotation, on one side the finger 21 of the platform does not come into contact with the spur 28 of the cannula slider, and on the other side, the pushing device 22 of the platform presses against the spur 31 of the guiding device 42 of the stylet slider. Thus, this slider is moved towards the back of the device, against the force of the spring 35 for propelling the stylet slider, until the retaining elements 32 of the support device of the stylet slider are arranged in the retaining device 33 for the stylet slider. The retaining device 33, for example in the shape of a ring, is similar to the retaining device 27 for the cannula slider, and the retaining elements 32, for example in the shape of hooks, are similar to the retaining elements 26 of the cannular slider. Advantageously, by providing the retaining device for the stylet slider in the form of a ring and the retaining elements of the stylet slider as hooks, coupling is easily and effectively provided as the hooks engage the ring through the hole. It should be noted that the retaining element of the stylet slider could be provided on the guide device 42 instead of being provided on the support device 41. Likewise, the index could rest on the support device instead of the guide device, as long as the displacement of the support device 41 leads to the displacement of the guide device 42.

At this stage, the device is triggered out and ready for the shot. The device is stable in the sense that the cannula and stylet slider hooks are maintained against the corresponding retaining elements. The arming button 15 is released and returns to its initial position under the effect of the return spring of the arming button. The platform 18 also returns to its initial position.

When the needle is armed, the sampling is started by a shot. This shot can be started by means of one of the triggers 37, 38 which have the function of releasing the displacement of the stylet and the cannula by releasing the stylet slider 30. The stylet slider is first propelled towards the front of the body under the force of the spring 35. During this propulsion, the fins of the guide device 42 follow the guide grooves provided in the body of the device. The displacement of the guide device leads to the displacement of the support device 41. The stylet 13 is guided by the cannula 14 with a small clearance in a plane perpendicular to the displacement direction of the needle. By means of this clearance it is possible to take into account the manufacturing tolerances of the different elements of the device of the invention.

Figure 3:
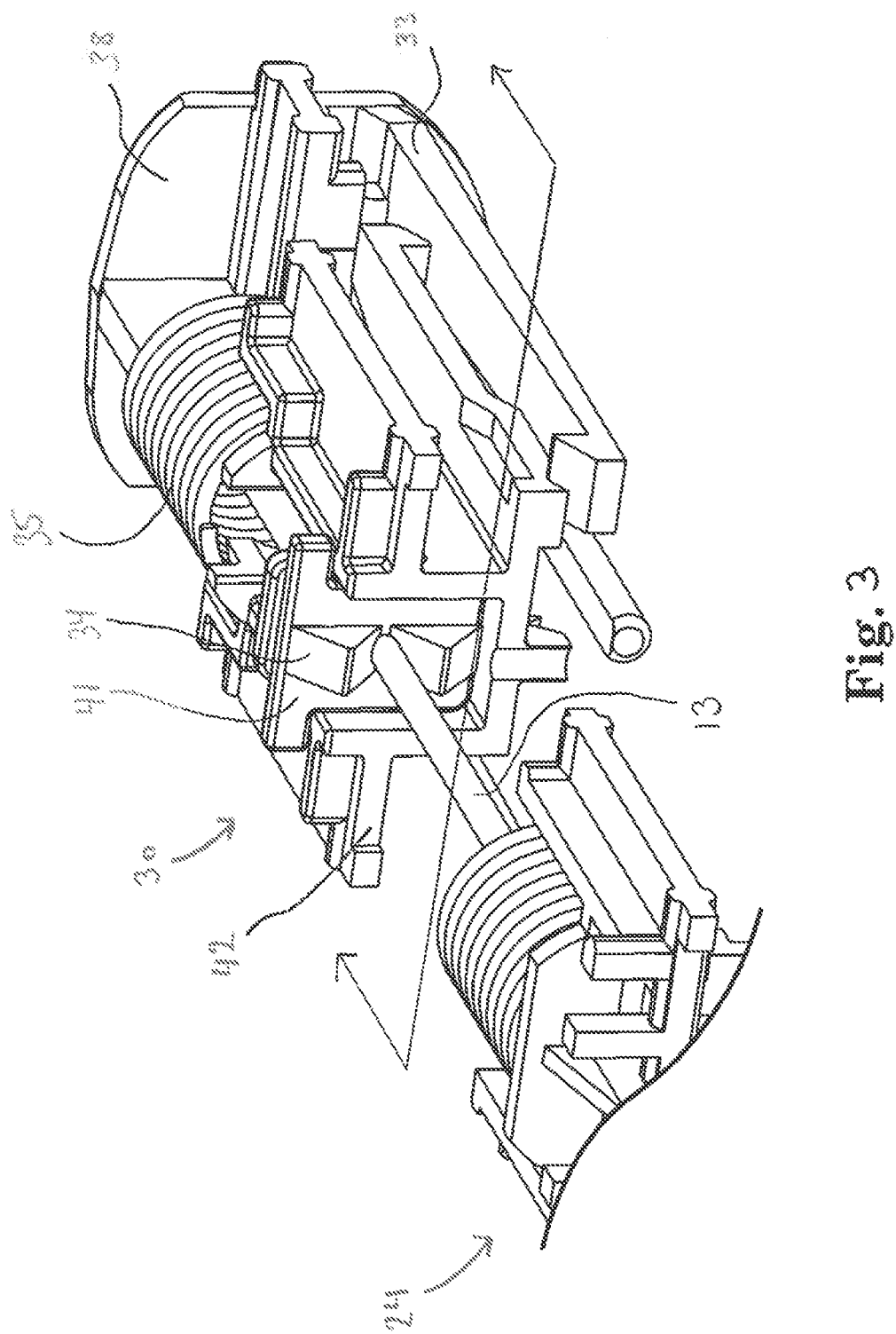
FIG. 3 is a perspective, sectional view of one embodiment of a stylet slider.

FIG. 3 is a partial, sectional view of the stylet slider 30 with the body 11 of the device 10 removed. The view additionally illustrates part of the cannula slider 24, the rear trigger 38 and a retaining device 33 of the stylet slider. The stylet slider 30 includes a support 41 and a guide 42. The support 41 is connected to the stylet 13. The stylet slider includes unlocking means 34.

Figures 4A, 4B:
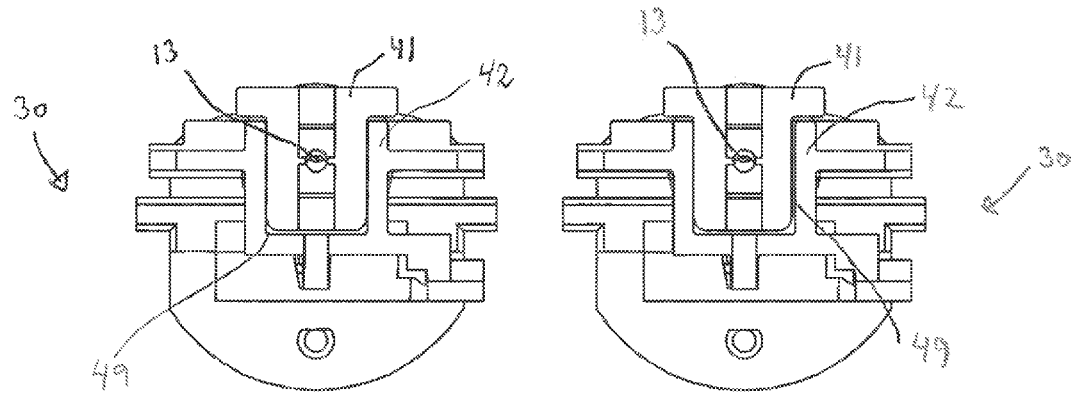
FIG. 4 A-4D are end views of different embodiments of a stylet slider.
Figures 4C, 4D:
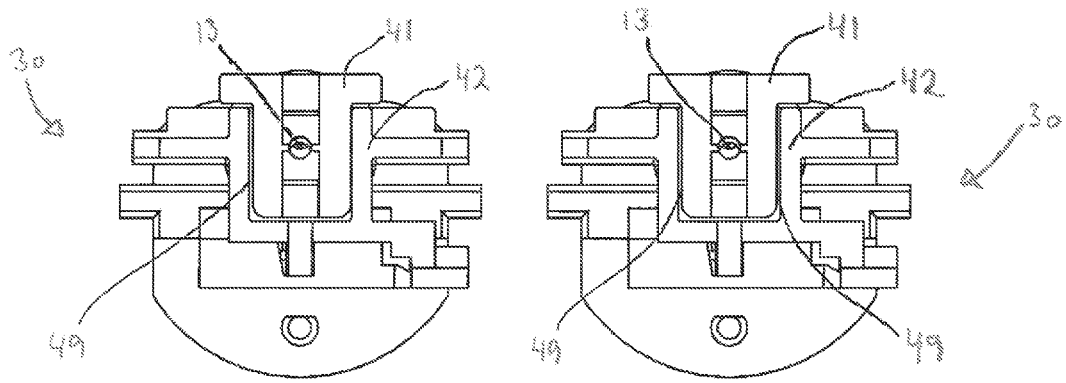

FIG. 4A is an end view of one embodiment of the stylet slider 30. The support 41 is connected to and supports the stylet 13. The support 41 is guided in the guide 42. The support 41 and the guide 42 are configured with a clearance 49 between them. The clearance is located in a plane perpendicular to the longitudinal axis of the needle to enable a relative displacement of the guide 42 and the support 41. In one embodiment illustrated in FIG. 4A, the clearance 49 is located below the support 41 and over the guide 42 in an "up/down" relationship. In the end views of the embodiments of FIGS. 4B, 4C and 4D, the clearance 49 is located between an outer side surface of the support 41 and an inner side surface of the guide 42 in a "sideways" relationship. In embodiments, the clearance 49 is located at outer side surfaces on each side of the support 41 and opposing inner side surfaces of the guide 42.

The cannula slider 24 is then propelled towards the front of the device under the force of the spring 29.

In the disclosed embodiment, the triggering mechanism comprises the two triggers and the rod 39 previously mentioned. The feature of having one of the triggers arranged in front of the body, in front of the tensioning button, and the other arranged in the rear of the body enables the user to easily access the triggering mechanism, whatever the position of the hand during the use of the device.

According to an advantageous embodiment, a security mechanism is provided for preventing a shot in case one of the triggers and in particular the front trigger is activated. Before the release of the shot, it is necessary to laterally displace the front trigger 37 in relation to the body 11 in order to remove the security function of the mechanism. After the shot, it is necessary to laterally re-displace the front trigger 37 in order to reactivate the security function. This security is manual in the sense that the user has the choice of activating the function by displacing the trigger, or not activating it.

To release the shot, it is necessary to press one of the triggers 37, 38, the front or the rear one. Actually, in the disclosed embodiment, the shot is always released by a displacement of the rear trigger 38. However, the front trigger and the rear trigger being linked by the rod 39, a pressure on the front trigger will result in the rear trigger being moved forward under the pressure of the rod. Thus, the mechanism can be used by pressing either the rear trigger or the front trigger.

When the rear trigger 38 is pressed, the unlocking means 41 being part of the rear trigger (or means for unlocking the stylet slider) comes into contact with the hooks of the stylet slider and displaces them towards each other. In this way, they are released from the retaining device 33 of the stylet slider. The slider 30 is propelled forward under the effect of the propulsion spring 35 of the stylet slider.

The means 34 for unlocking the cannula slider comes into contact with the hooks of the cannula slider, presses these hooks towards the centre and releases the retaining elements 27 of the cannula slider. The cannula slider 24 advances under the effect of the propulsion spring 29 of the cannula. This slider advances until it arrives at a stop provided in the body of the device. At this stage, the shot is completed and the device can be withdrawn from the organ from which samples have been taken.

After the arming of the stylet, the platform 18 has returned to its rest position under the effect of the return device of the platform. After the shot, the pieces composing the device return to their initial positions. The sample taken is confined between the stylet 13 and the cannula 14, in the notch provided for this purpose. The sample can be retrieved by retracting the cannula, for example by carrying out an arming movement as previously explained. When the arming of the cannula is completed, it is possible to retrieve the sample. If a new sampling has to be carried out, the arming button is operated so as to arm the device completely and make it ready for the shot. If it is not necessary to take a new sample, the arming is carried out as well and a blank shot is made.

The present invention has several advantages in comparison with the devices of the prior art. In particular, by the setup of the retaining elements 26, 32 of the stylet and cannula sliders, it is possible to provide at least two symmetrical hooks. The forces applied on these hooks to hold them by the retaining means as well as during their unhooking during a shot are symmetrical. On the one hand, this ensures that there is no flexion and/or twist on the needle, and on the other hand, this enables a safer support of the hooks.

The clearance between the guide device 42 and the support device 41 forming the stylet slider also ensures an optimal displacement of the stylet in relation to the cannula and thus prevents the jamming or deformation of the needle.

According to an advantageous embodiment, the needle is off-center towards the bottom of the device 10. This enables the use of the device in an easier way with another apparatus as for example an echographic probe.

The device according to the invention can be operated by one single hand, since the arming of the cannula and the arming of the stylet use the same arming button.

By the symmetrical construction of the retaining elements of the cannula and stylet sliders and by the position of the propulsion springs of these sliders, the stresses are divided symmetrically around the axis of the needle. Thus, the risks of jamming between the stylet and the cannula are minimized, which enables the device to be used several times and thus allows for a greater number of samples to be taken.

The reduction of the risk of jamming and the provision of the stylet slider in two elements that have a clearance between each other allow for the reduction of the force of the propulsion springs while maintaining a high displacement speed for the sliders. This is advantageous for the user because a smaller force is necessary for arming the device. The handling with a single hand is easier in this way.

Using guide grooves provided in the body of the device and slider fins moving in these grooves also ensures an optimal guidance and reduces the jamming risk.

The invention claimed is:

1. A device for taking a sample of soft tissue from an organ, said device comprising:

a body and a needle arranged in the body and extending at least partly outside the body through a front end of the body, the needle is formed by a stylet and a cannula coaxial with said stylet along a longitudinal axis of the needle, the cannula coupled to a cannula slider comprising a first retaining element for maintaining the cannula slider in a shooting position, the stylet coupled to a stylet slider comprising a second retaining element for maintaining the stylet slider in a shooting position;

an arming button manipulable to sequentially move the cannula slider and subsequently move the stylet slider from a rest position to the shooting position, thereby moving the stylet and the cannula towards a rear end of the body;

a trigger mechanism configured to release the stylet slider, which in sequence releases the cannula slider to displace the stylet and the cannula from the shooting position to the rest position;

wherein the stylet slider comprises a support integral with the stylet and a guide movable in the body of the device, and wherein the support and the guide are configured with a clearance between each other in a plane perpendicular to the longitudinal axis of the needle to enable a relative displacement of the guide and the support.

2. The device according to claim 1, wherein the arming button is integral with a platform, the platform configured to cooperate with the guide of the stylet slider to move the stylet towards the rear end of the body during the arming of the stylet.

3. The device according to claim 2, wherein the platform is configured to pivot around a pivot axis integral with the arming button, and wherein a first end of the platform that is located closer to the front end of the body than an opposite second end of the platform comprises a zone that is wider than the second end of the platform, the zone comprising one finger at opposite sides of the zone.

4. The device according to claim 3, wherein the cannula slider comprises a first spur configured to cooperate with one of the fingers of the platform.

5. The device according to claim 2, wherein a second end of the platform that is located closer to the rear end of the body than an opposite first end of the platform comprises a pushing device configured to cooperate with a second spur attached to the guide of the stylet slider.

6. The device according to claim 1, wherein the support of the stylet slider comprises two or more hooks arranged symmetrically in relation to a longitudinal axis of the needle, the hooks configured to cooperate with a retaining device of the stylet slider, the retaining device forming part of the body.

7. The device according to claim 1, wherein the support of the stylet slider comprises an unlocking device arranged to displace the first retaining element of the cannula slider and to unhook the first retaining element from a retaining device of the cannula slider.

8. The device according to claim 7, wherein the unlocking device is provided at a front end of the support and comprises two inclined planes configured for unlocking the cannula slider.

9. The device according to claim 1, wherein the displacement of the stylet from the shooting position to the rest position is caused by a spring for propelling the stylet slider, the spring placed between the support and a retaining device for the stylet slider.

10. The device according to claim 1, wherein the support is overmolded on the stylet.

11. The device according to claim 1, wherein the arming button cooperates with a return spring configured to bring back the arming button to a rest position relatively closer to the front end of the body when the arming button is not being manipulated.

* * * * *